United States Patent
Lindgren

(10) Patent No.: US 6,238,419 B1
(45) Date of Patent: May 29, 2001

(54) HEART STIMULATING DEVICE HAVING FUSION AND PSEUDOFUSION HEARTBEAT DETECTION CAPABILITY

(75) Inventor: Anders Lindgren, Täby (SE)

(73) Assignee: Pacesetter AB, Järfälla (SE)

(*) Notice: Subject to any disclaimer, the term of this patent is extended or adjusted under 35 U.S.C. 154(b) by 0 days.

(21) Appl. No.: 09/355,187
(22) PCT Filed: Jan. 29, 1998
(86) PCT No.: PCT/SE98/00133
  § 371 Date: Jul. 28, 1999
  § 102(e) Date: Jul. 28, 1999
(87) PCT Pub. No.: WO98/34680
  PCT Pub. Date: Aug. 13, 1998

(30) Foreign Application Priority Data

Feb. 5, 1997 (SE) .................................................... 9700396

(51) Int. Cl.$^7$ .................................................... A61N 1/362
(52) U.S. Cl. .................................................... 607/9
(58) Field of Search .................................. 607/9, 14, 17, 607/18, 19, 20

(56) References Cited

U.S. PATENT DOCUMENTS 5,267,560  12/1993  Cohen .
5,534,016   7/1996  Boute .

*Primary Examiner*—Scott M. Getzow
(74) *Attorney, Agent, or Firm*—Schiff Hardin & Waite

(57) ABSTRACT

A heart stimulating device has the capability of detecting fusion and/or pseudofusion heartbeats by measuring electrical impedance encountered by a delivered stimulation pulse. The device has a pulse generator connected to a lead system for emitting and delivering stimulation pulses, and an impedance measuring arrangement for measuring the impedance. A logic circuit determines that a response by the cardiac tissue to a delivered stimulation pulse includes a fusion or pseudofusion heartbeat if the measured electrical impedance is within a predetermined impedance range, and determines that the response does not include a fusion and/or pseudofusion heartbeat if the measured electrical impedance is outside of the predetermined impedance range.

5 Claims, 3 Drawing Sheets

HEART STIMULATING DEVICE HAVING FUSION AND PSEUDOFUSION HEARTBEAT DETECTION CAPABILITY

BACKGROUND OF THE INVENTION

1. Field of the Invention

The present invention relates to a heart stimulating device having the capability to detect the occurrence of fusion and pseudofusion heart beats, i.e. delivery of electrical stimulation pulses simultaneously or with a small separation in time from spontaneous heart beats.

2. Description of the Prior Art

Fusion beats generally refers to a situation where atrial or ventricular depolarization starts from two different positions in the heart. Such a situation arises when a natural heart beat occurs simultaneously with an electrical stimulation pulse from a heart stimulating device and they both contribute to the depolarisation of a heart chamber.

Pseudofusion beats generally refers to a situation where atrial or ventricular depolarization starts spontaneously in the heart and a stimulation pulse is delivered subsequently and does not contribute to the depolarization.

In demand pacemakers or other heart stimulating devices that aim to electrically stimulate a patient's heart only in the absence of normal intrinsic activity, fusion beats or pseudofusion beats present a particular problem, since intrinsic events are to be favoured and stimulation energy is to be saved until really needed. In that way the longevity of a battery powered heart stimulation device is improved.

Some terminology used conventional is explained below.

Impedance: The total resistance to the flow of electrical current through a conductor, including resistance produced by tissue and electronic components including resistors, capacitors and coils. In pacing, impedance and resistance are sometimes used interchangeably, but strictly speaking, impedance involves a time-dependent relationship between voltage and current, whereas resistance is a fixed number. Resistance and impedance is usually stated in ohms.

IEGM: An abbreviation for intracardiac electrogram. IEGM signals are emitted by active cardiac tissue and sensed through electrodes placed on or within the heart.

QRS or QRS complex: The ventricular depolarization as seen on the electro cardiogram or in the IEGM signals.

Intrinsic: Inherent or belonging to the heart itself. An intrinsic beat is a naturally occurring heart beat.

R wave: an intrinsic ventricular event. R refers to the entire intrinsic QRS complex.

Evoked response: The electrical activation of the myocardium by a pacemaker output pulse. The ability of cardiac tissue to respond depends on its activity state.

Ventricular fusion beat: the pacemaker impulse appears close to a spontaneous QRS complex and partly contributes to the ventricular depolarization.

Ventricular pseudofusion beat: the pacemaker impulse appears within a spontaneous QRS complex and does not contribute to the ventricular depolarization.

Atrial fusion beat: the pacemaker impulse appears close to a spontaneous P wave and partly contributes to the atrial depolarization.

Atrial pseudofusion beat: the pacemaker impulse appears within a spontaneous P wave and does not contribute to the atrial depolarization.

A fusion or pseudofusion beat, either in a ventricle or an atrium, may be referred to as simply a fusion beat in contexts where problems related thereto are similar to those of regular fusion beats.

In conventional pacemakers, pulses may be delivered although intrinsic heart activity is present at a rate close to that of the pacemaker. Moreover, backup pulses may by delivered by the pacemaker for safety reasons when an evoked response is rendered undetectable by a fusion or pseudofusion beat. In these and other cases, the detection of evoked response is disturbed by intrinsic heart activity. Further, in order to detect lead breakage or other anomalies, such a pacemaker may be provided with means to determining a measure of the impedance of the lead arrangement by measuring voltage at leading and trailing edges of a delivered stimulation pulse.

Conventional pacemakers still need improvement to effectively overcome the problem of consuming the battery energy prematurely due to failure to favor present intrinsic activity in the heart. Detection of fusion and pseudofusion beats present a general problem in the art.

SUMMARY OF THE INVENTION

It is an object of the present invention to provide a heart stimulation device which has the capability of detecting fusion and/or pseudofusion heartbeats. Consistent with this object, it is a further object of the present invention to provide a device for reliably detecting fusion and/or pseudofusion heartbeats by means of impedance measurements. It is a further object to employ the detection of fusion and/or pseudofusion heartbeats to enable a reduction of the energy used for stimulating a heart.

The inventor has conducted extensive experimental studies which have revealed that an impedance encountered by an electrical stimulation pulse delivered to the heart systematically takes lower values if the heart is intrinsically stimulated at the same time or within a small separation in time, i.e., in case of fusion/pseudofusion heart beats.

Consistent with these experimental studies the above objects are achieved in accordance with the principles of the present invention in a heart stimulator having a pulse generator and a lead arrangement which emit and deliver stimulation pulses to cardiac tissue, and an impedance measuring arrangement which measures an electrical impedance as "seen" by the delivered stimulation pulses, and having a logic circuit which identifies whether a response by the cardiac tissue to a delivered stimulation pulse includes a fusion and/or a pseudofusion heartbeat, by determining such a fusion or pseudofusion heartbeat to be present if the measured electrical impedance is within a predetermined impedance range, and determining that a fusion or pseudofusion heartbeat is not present if the measured electrical impedance is outside of the aforementioned predetermined impedance range.

DESCRIPTION OF THE PREFERRED EMBODIMENTS

Figure 1:
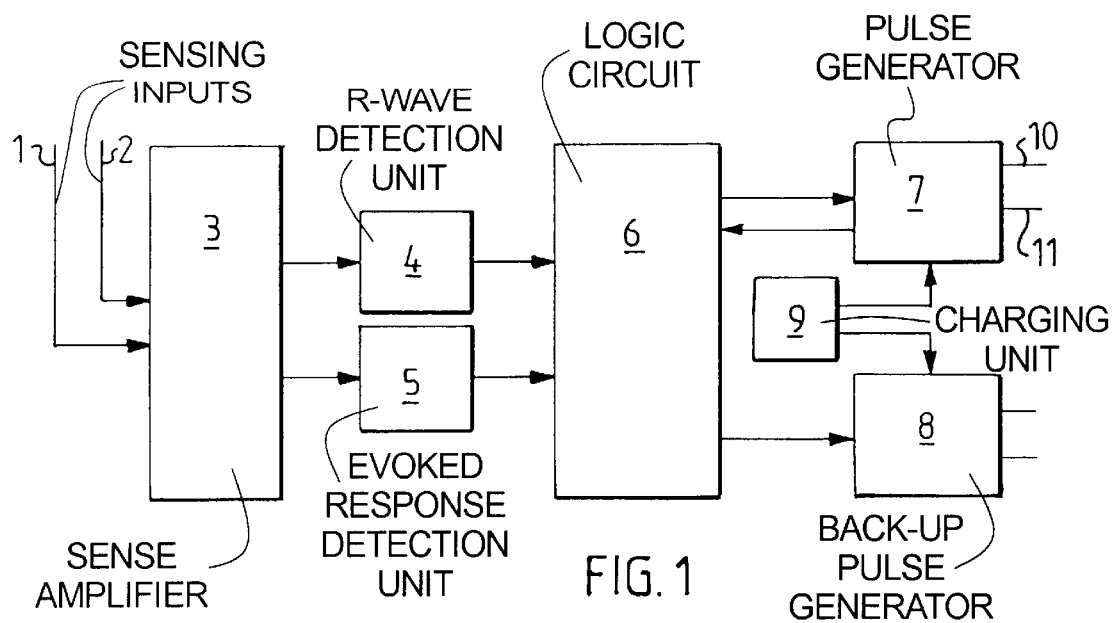
FIG. 1 is a block diagram of a heart stimulating device according the invention including, a pulse output stage having the ability to measure impedance and a logic circuit having the ability to detect fusion and pseudofusion beats based on the measured impedance.

FIG. 1 shows an embodiment of a heart stimulating device according the invention. The described type of device is operable to inhibit stimulation to favour intrinsic events. The device has sensing input 1, 2 that feed IEGM signals to a sense amplifier 3. The sensing inputs 1, 2 are to be connected to a cable (not shown) and a cardiac electrode (not shown) which provide the IEGM signals to the heart stimulating device. The sense amplifier provides amplified IEGM signals to two detection units 4, 5. A filtered first R wave detection units 4 is operable to detect intrinsic QRS complexes. An evoked response (ER) detection units 5 is operable to detect stimulation-evoked QRS complexes. Each of the detection units 4, 5 is connected to a logic circuit 6 to which it indicates a detected QRS complex.

The logic circuit 6 controls a pace pulse generator 7 and a back-up pulse generator 8 which are operable to transmit stimulation pulses to a patient's heart. A charging unit 9 is connected to both pulse generators 7, 8 to provide them with the necessary stimulation energy. The pulse generators 7, 8 are to be connected via the same cable (not shown) to the same cardiac electrode (not shown) as the sense amplifier 3. However, it is preferred that the sense amplifier 3 has a bipolar mode of operation and the pace pulse generator 7 has a unipolar mode of operation. In the case of a unipolar heart stimulator, a conductive casing (not shown) of the heart stimulating device functions as one pole and a cardiac electrode as the other.

Further, the pace pulse generator 7 includes a measuring arrangement for measuring an impedance encountered by a stimulation pulse when delivered. In this embodiment, such the result of such a measurement is fed to the logic circuit 6 for determination whether or not the delivered stimulation pulse gave rise to a fusion beat or a pseudofusion heart beat. The operation of the measuring arrangement is controlled by the logic circuit 6, which also includes timing means in order to stimulate the patient's heart at an appropriate rate that can be based on detections made in the detection unit 4, 5.

Additionally or alternatively, the inventive heart stimulation device could include means for detecting P waves and atrial evoked response in a manner similar to what is indicated above for ventricular operation.

With reference to FIG. 2 an explanation will be given to different events taking place in a heart as seen on an ECG plot. Curve 20 shows an spontaneous or intrinsic beat without any pacemaker pulse being delivered. A QRS complex is seen as a peak at 21 and repolarization occurs at 22. Curve 23 shows a beat evoked entirely by a stimulation pulse delivered by the heart stimulating device without any intrinsic heart activity leading to ventricular contraction. A pulse is delivered at 24 (width and hight not drawn to scale) which results in a QRS complex at 25 followed by repolarization at 26.

In the case of curve 27, a pulse 28 is delivered at the start of a spontaneous ventricular depolarization, i.e., somewhat earlier. A QRS complex 29 displays increased width and a change in the appearance of the T wave 30. This suggests that part of the ventricle was depolarized by the stimulation pulse 28, but that the heart also was depolarized by spontaneous conduction. The result is a fusion beat.

Despite the appearance of the stimulation pulse 32 in curve 31, the following QRS complex 33 and the repolarization 34 has a configuration typical of spontaneous depolarization. The stimulation pulse 32 obviously occurs too late to affect the ongoing depolarization. This results in a pseudofusion beat.

It has been surprisingly found that the impedance encountered by a delivered stimulation pulse differs considerably in the situation of curve 23, wherein the heart activity is controlled only by the stimulation, and the situations of curves 27 and 31, showing fusion and pseudofusion beats, respectively. Impedance decreases of at least 30 ohms, and seemingly about 200 ohms, have been measured in the fusion and pseudofusion heart beats compared to the purely stimulated beats.

Figure 3:
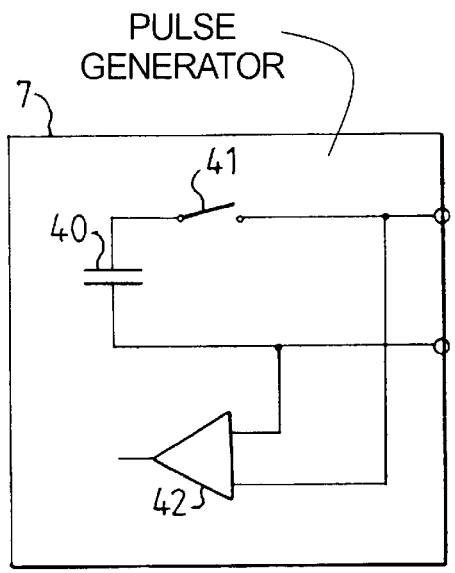
FIG. 3 shows schematically one embodiment of a pulse output stage in the device of FIG. 1 including voltage measuring circuitry.

FIG. 3 shows known circuitry for measuring impedance in cardiac leads (cable and electrode). The measuring circuitry is incorporated in the pulse generator 7 and includes a capacitor 40 connected to terminal 10 through a switch 41 and to terminal 11. A voltage measuring unit for measuring the voltage across terminals 10 and 11 is indicated by 42.

Figure 4:
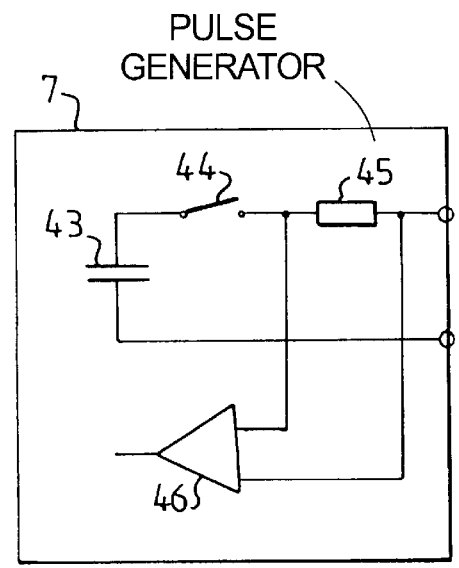
FIG. 4 shows schematically another embodiment of a pulse output stage in the device of FIG. 1 including voltage measuring circuitry.
Figure 2A:
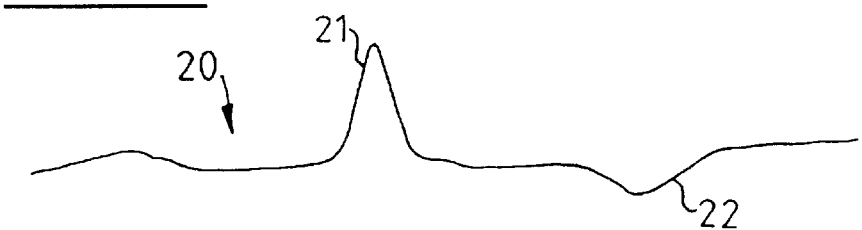
FIGS. 2a, 2b, 2c and 2d respectively show examples of ICG signals that indicate the occurrence of a spontaneous beat, a paced beat, a fusion beat, and a pseudofusion beat.
Figure 2B:
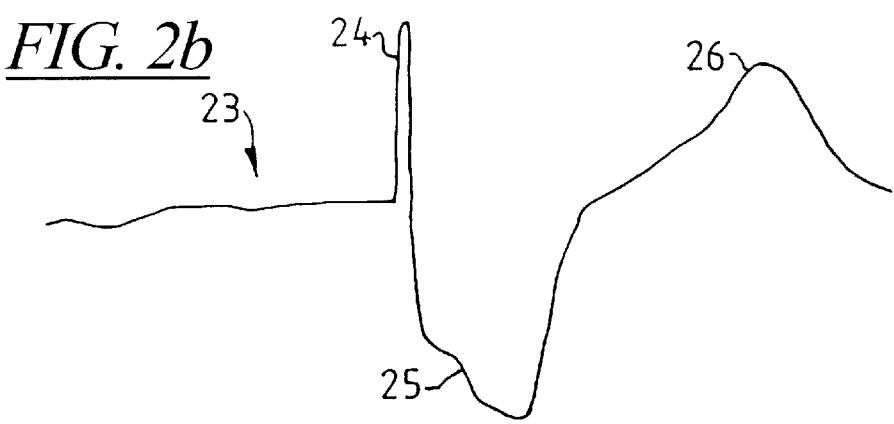
Figure 2C:
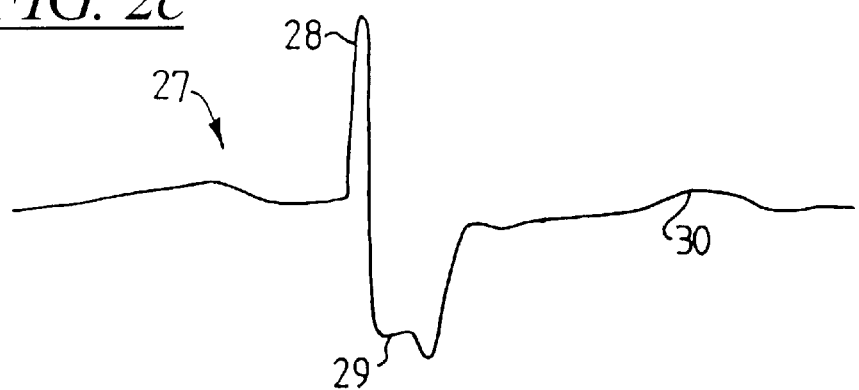
Figure 2D:
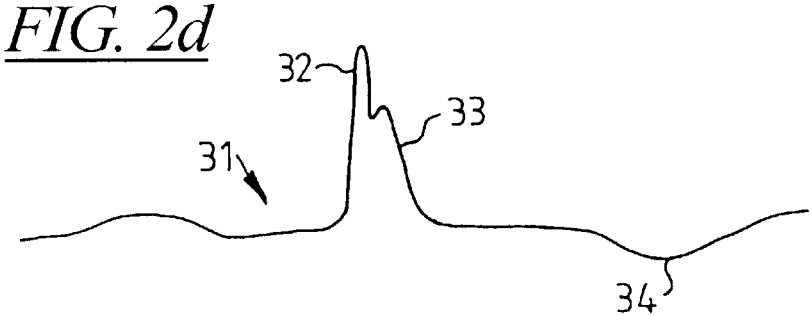

FIG. 4 shows alternative known circuitry for measuring impedance in cardiac leads. The circuitry includes a capacitor 43 connected to terminal 10 through a switch 44 and a low ohm resistor 45 and to terminal 11. A voltage measuring unit for measuring the voltage resistor 45 is indicated by 46.

Naturally, combinations of the circuitry of FIGS. 3 and 4 could be used for the impedance measuring means in the invention.

Figure 5:
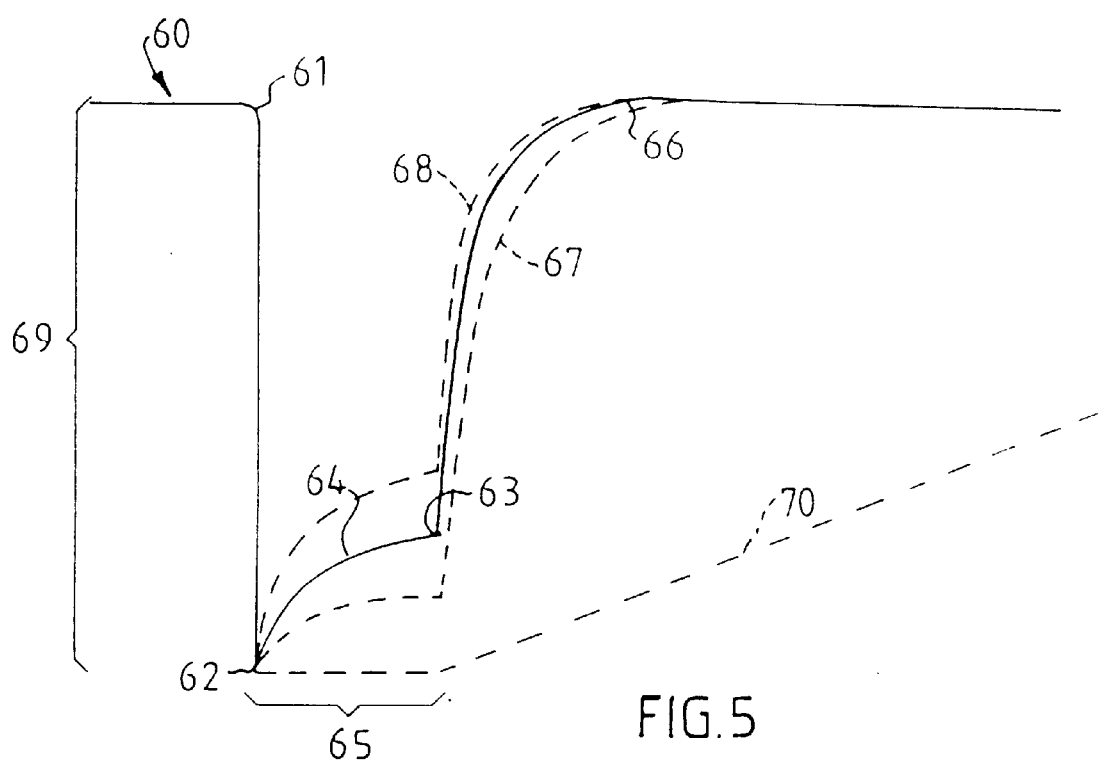
FIG. 5 shows as a solid line a shape that a stimulation pulse would have for a given impedance and, by dashed lines, alternate shapes corresponding to different impedances.

References will now be made to FIG. 5. Curve 60 shows details of a reference stimulation pulse as it could be sensed as IEGM signals in a heart stimulating device according to the invention. A delivery of a stimulation pulse begins at 61. The signal level changes momentarily to 62 from which point a discharge of the stimulation energy proceeds to point 63 along a curve segment 64 that can be approximated by an RC discharge curve. The length 65 of the pulse is in the order of 0.5 ms. After the pulse, the signal resumes its voltage level at 66.

Once an implanted cardiac electrode assumes a stable position in the heart, its impedance will be rather constant under normal stimulating conditions undisturbed by intrinsic activity. A typical value is 500 ohms. In FIG. 5, pulse delivery under such a normal impedance circumstances is represented by dashed curve 67 oriented below curve segments between points 62 and 66. Dashed curve 68 represents a lower impedance of about 300 ohms which indicates the occurrence of a fusion or pseudofusion beat. In dashed curve 70, no discharge of the pulse energy occurs during the pulse. Thus, there is an indication of lead break or similar. The signal magnitude 69 of the stimulation pulse in FIG. 5 is about 5 V.

The circuitry of FIGS. 4 and/or 5 is sued to determine whether the impedance encountered by the stimulation pulse belongs to a range below or above a reference value (corresponding to curve 64, FIG. 5). If the impedance is found to be below the reference, an indication of a fusion/pseudofusion beat is presented in the logic means of the device. If the impedance is found to be equal to or above the reference, an indication of the absence of a fusion/pseudofusion beat is presented in the logic means of the device.

The presently preferred arrangement for measuring the impedance that a stimulating pulse encounters when delivered to the heart includes a resistor connected in series in the electrical circuit for effecting the pulse. Such a resistor has a low resistance not to dissipate energy unnecessarily but enough to provide a signal for measurement. The impedance is calculated from the relationship between resistor current and pulse voltage in a well-known manner. It is further preferred that the measurement be made during a short interval only immediately following point 62 in FIG. 5. However, the current (voltage across known resistor) and/or voltage could be measured in one or several points along the pulse curve to obtain an impedance measure. One specific alternative is to measure the voltage in the points 62 and 63 of FIG. 5 so as to obtain an impedance measure.

It should be noted that the figures may not be drawn to scale but are rather intended to illustrate functions and qualities of the invention and electrical signals relating to its operation. Further, it is to be understood that this embodiment description includes merely illustrative examples of the application of the invention. For instance, the invention is applicable in atrial as well as ventricular fusion and pseudofusion beat detection. Many variations and modifications may be made without departing from the scope of the invention as defined by the appended claims.

What is claimed is:

1. Heart stimulating device comprising a pulse generator adapted to deliver a stimulation pulse to a heart, an impedance measuring arrangement which measures an electrical impedance encountered by said delivered stimulation pulses, and a logic circuit connected to said impedance measuring arrangement which identifies a response to one of said stimulation pulses as including a fusion or pseudofusion heartbeat if the measured electrical impedance is within a predetermined impedance range, and which identifies the response to the delivered stimulation pulse as not including a fusion or pseudofusion heartbeat if the measured electrical impedance is not within said predetermined impedance range.

2. The heart stimulating device of claim 1, wherein the impedance measuring arrangement determines the impedance by measuring a stimulation pulse voltage of a stimulation pulse delivered by the pulse generator.

3. The heart stimulating device of claim 2, wherein the impedance measuring arrangement measures the voltage at least twice during a stimulation pulse.

4. The heart stimulating device of claim 1, wherein the impedance measuring arrangement determines the impedance by measuring a stimulation of pulse current of a stimulation pulse delivered by the pulse generator.

5. The heart stimulating device of claim 4, wherein the impedance measuring arrangement measures the current at least twice during a stimulation pulse.

* * * * *